US011471307B2

(12) United States Patent
Penot

(10) Patent No.: US 11,471,307 B2
(45) Date of Patent: Oct. 18, 2022

(54) FOOT PROSTHESIS COMPRISING A DAMPING ELEMENT

(71) Applicant: PM Ingenierie Et Design, Villebon-sur-Yvette (FR)

(72) Inventor: Benjamin Penot, Villebon-sur-Yvette (FR)

(73) Assignee: PM INGENIERIE ET DESIGN, Villebon-sur-Yvette (FR)

(*) Notice: Subject to any disclaimer, the term of this patent is extended or adjusted under 35 U.S.C. 154(b) by 144 days.

(21) Appl. No.: 16/494,408

(22) PCT Filed: Mar. 9, 2018

(86) PCT No.: PCT/EP2018/055868
§ 371 (c)(1),
(2) Date: Sep. 16, 2019

(87) PCT Pub. No.: WO2018/166905
PCT Pub. Date: Sep. 20, 2018

(65) Prior Publication Data
US 2020/0085596 A1 Mar. 19, 2020

(30) Foreign Application Priority Data

Mar. 17, 2017 (FR) ...................................... 1752217
Nov. 29, 2017 (FR) ...................................... 1761388

(51) Int. Cl.
*A61F 2/66* (2006.01)
*A61F 2/50* (2006.01)
*A61F 2/30* (2006.01)

(52) U.S. Cl.
CPC ...... *A61F 2/66* (2013.01); *A61F 2002/30604* (2013.01); *A61F 2002/5003* (2013.01);
(Continued)

(58) Field of Classification Search
CPC ................ A61F 2/66; A61F 2002/5003; A61F 2002/30604; A61F 2002/3064;
(Continued)

(56) References Cited

U.S. PATENT DOCUMENTS 2,475,373 A * 7/1949 Catranis .................... A61F 2/66
623/49
2,749,557 A 6/1956 Riddle
(Continued)

FOREIGN PATENT DOCUMENTS

DE 102004062957 A1 * 7/2006 ............... A61F 2/66
DE 102014006571 B3 8/2015
(Continued)

OTHER PUBLICATIONS

International Search Report or PCT Application No. PCT/EP2018/055868 dated May 8, 2018.

*Primary Examiner* — Christie L Bahena
(74) *Attorney, Agent, or Firm* — McCormick, Paulding & Huber PLLC

(57) ABSTRACT

The present invention relates to a foot prosthesis (1, 61) comprising a heel (6, 71) and a tip (7, 62), both of which can bear on the ground, and an ankle support (2, 67), characterised in that the prosthesis also comprises at least one damping element (10, 76) designed to be at a distance from the ground.

20 Claims, 6 Drawing Sheets

(52) U.S. Cl.
CPC ............. *A61F 2002/6621* (2013.01); *A61F 2002/6642* (2013.01); *A61F 2002/6657* (2013.01)

(58) Field of Classification Search
CPC ...... A61F 2002/6607; A61F 2002/6621; A61F 2002/6642; A61F 2002/6657
See application file for complete search history.

(56) References Cited

U.S. PATENT DOCUMENTS

| | | | |
|---|---|---|---|
| 6,767,370 B1* | 7/2004 | Mosier | A61F 2/66 623/55 |
| 2005/0033450 A1 | 2/2005 | Christensen | |
| 2008/0306612 A1* | 12/2008 | Mosier | A61F 2/66 623/55 |
| 2009/0037000 A1* | 2/2009 | Frye, Jr. | A61F 2/60 623/33 |
| 2010/0023135 A1 | 1/2010 | Rubie et al. | |
| 2012/0191220 A1 | 7/2012 | Bedard et al. | |
| 2014/0379096 A1* | 12/2014 | Zahedi | A61F 2/64 623/25 |

FOREIGN PATENT DOCUMENTS

| | | |
|---|---|---|
| EP | 0280004 A1 | 8/1988 |
| EP | 0487852 A1 | 6/1992 |
| WO | 9641598 A1 | 12/1996 |
| WO | 2011066354 A2 | 6/2011 |

* cited by examiner

FOOT PROSTHESIS COMPRISING A DAMPING ELEMENT

CROSS-REFERENCE TO RELATED APPLICATION

This application is a National Stage application of International Patent Application No. PCT/EP2018/055868 filed on Mar. 9, 2018, which claims priority to French Patent Application No. 1752217 filed on Mar. 17, 2017 and French Patent Application No. 1761388 filed Nov. 29, 2017, each of which is hereby incorporated by reference in its entirety.

TECHNICAL FIELD

The present invention relates, generally speaking, to a foot prosthesis comprising a damping element having a shape close to that of a human foot. The objective of the invention is notably to increase the lifetime of this type of prosthesis and also to improve the walking comfort of the user thereof.

BACKGROUND OF THE INVENTION

Nowadays, foot prostheses constitute a technical solution for replacing an amputated foot that cannot be circumvented. Foot prostheses such as those described in the documents WO9641598, EP0280004 or U.S. Pat. No. 2,749,557, which seek to reproduce the anatomy of a human foot, are known from the prior art but the main drawback of these prostheses is that they do not make it possible to reproduce the complexity of the different movements made by a foot. For example, the patent U.S. Pat. No. 2,749,557 describes an ankle system enabling the adjustment of the height of the heel of the prosthesis as well as the positioning of the foot tip. The major drawback of this system is that it only enables adjustment on a limited number of positions. What is more, this foot prosthesis solution does not enable either an energy restoration or management of inversion and reversion. Foot prostheses comprising a spring blade, made of composite material of the carbon, glass or aramid fibre type, also exist in the prior art, making it possible to restore the energy stored up during the phase of the prosthesis bearing on the ground. This type of prosthesis seeks to reproduce the movements of a human foot during phases of bearing on the ground or relaunching the body. Such a prosthesis is described, for example, in the patent application WO2011066354. The major drawback of these prostheses is that it is necessary to add onto the spring blade various elements making it possible to reproduce the aestheticism and the anatomy of a human foot. Furthermore, foot prostheses implementing a simple bearing plate also exist. An active system, known as electronic prosthesis, equipped with sensors, is then used notably making it possible to detect the bearing on the ground, and comprising actuators on the ankle and the knee making it possible to re-tauten the foot. This type of system is described, for example, in the patent application US 2012/0191220.

The various protheses known at present do not make it possible to reproduce the kinematics of a human foot in a satisfactory manner. Indeed, walking mobilises certain muscular groups during the bearing phase, making it possible to dampen the impact of the step, and other muscular groups during the propulsion phase, enabling energy restoration. Blade protheses enable relatively efficient accumulation and restoration of energy but, on the other hand, they have the drawback of not being able to adapt correctly to a ground having a considerable banking or on which protuberances are present, such as pebbles or stones. Moreover, they have a tendency to wear rapidly on account of the friction generated by the permanent contact of the prosthesis on the ground.

The aim of the invention is thus to improve the lifetime of foot prostheses and to increase the walking comfort of the user.

SUMMARY OF THE INVENTION

To do so, the subject matter of the invention is notably a foot prosthesis comprising a heel and a foot tip capable of bearing on the ground and an ankle support, said foot prosthesis being remarkable in that it further comprises at least one damping element configured to be distant from said ground.

Preferably, the damping element connects the foot tip to the ankle support.

According to an aspect of the invention, the foot prosthesis further comprises an instep connecting the foot tip to the ankle support.

Preferably, the foot prosthesis further comprises a means for accumulating and restoring energy arranged between the foot tip and the instep.

Advantageously, the foot prosthesis comprises a connecting rod connecting the instep to the heel.

Further preferably, the damping element comprises a first curvature point and a second curvature point.

Preferably, the damping element comprises one end connected to the ankle support by the outside of the foot prosthesis.

According to another aspect of the invention, the damping element comprises one end connected to the ankle support by the inside of the foot prosthesis.

Advantageously, the ankle support further comprises an adjustment means arranged outside or inside the ankle support.

In another aspect of the invention, a robot comprises a foot prosthesis according to the invention.

BRIEF DESCRIPTION OF DRAWINGS

The invention will be better understood on reading the description that follows, made with reference to the appended figures, in which.

DETAILED DESCRIPTION

Figure 1:
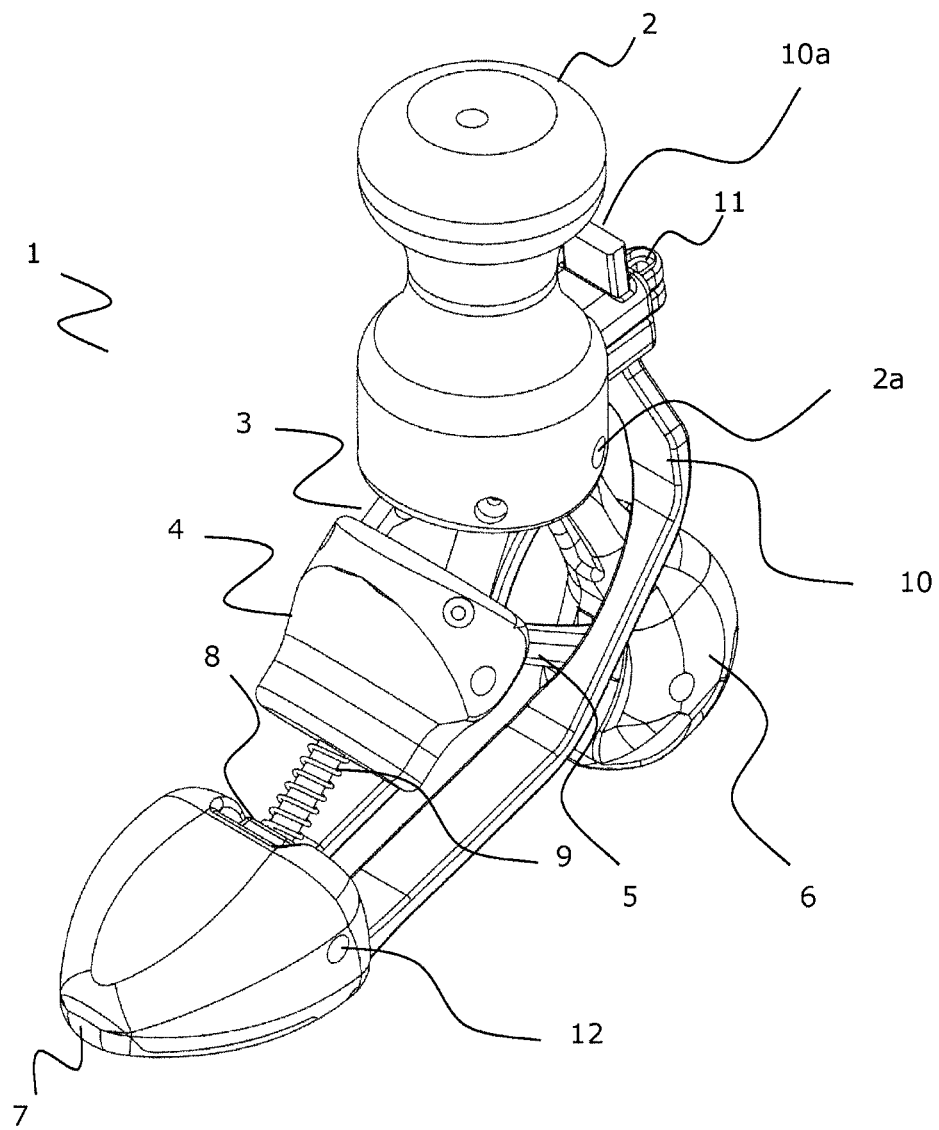
FIG. 1 is a perspective view of an example of foot prosthesis according to the invention configured to receive a flat heeled shoe.
Figure 5:
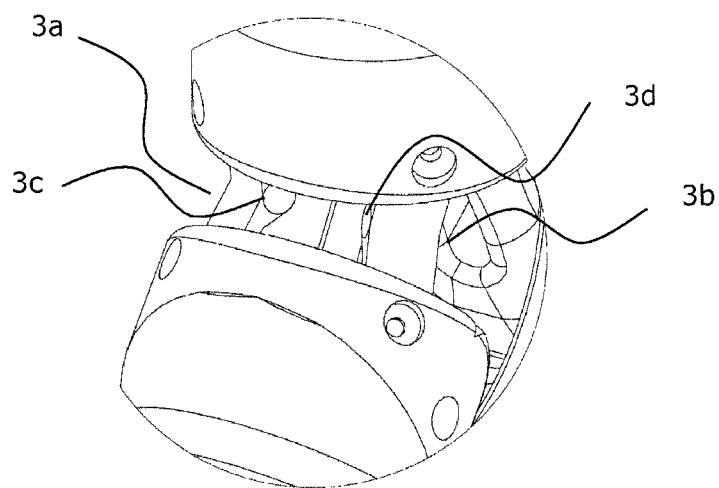
FIG. 5 is a detail view of another mechanism of the prosthesis shown in FIG. 1.

In FIG. 1 is represented an exemplary embodiment of the foot prosthesis 1 according to the invention comprising an ankle support 2, enabling the foot prosthesis 1 to fit onto the tibia of the patient, connected on its lower part to an instep 4 through a mechanism 3. As may be better seen in FIG. 5, this mechanism 3 comprises a first pair of tie rods 3*a* situated inside the foot prosthesis 1 and a second pair of tie rods 3*b* situated outside the foot prosthesis 1. The first pair of tie rods 3*a* is hinged around a pivot link 3*c* and the second pair of tie rods 3*b* around a pivot link 3*d*. Also in FIGS. 1 and 2 may be seen a tie rod 5 hinged with the instep 4 by means of the axis 5*a*, of pivot link type, and with the heel 6 by means of the axis 5*b*, also of pivot link type. This tie rod 5 makes it possible to transfer the force coming from the heel 6, when said heel is laid on the ground, to the instep 4. The heel 6 is also hinged with the ankle support 2 by means of an axis 2*a* of pivot link type. The foot prosthesis 1 also comprises a foot tip 7 connected to the instep 4 through a universal joint type link 8. This universal joint 8 comprises a first hinge 8*a* of pivot link type forming a first axis orthogonal to the plane of symmetry of the foot tip 7 and a second hinge 8*b* of pivot link type forming a second axis. The second hinge 8*b* further comprises a spring 9. In other embodiments, the spring 9 may be replaced by a hydraulic or pneumatic dampener, or any other means making it possible to obtain stiffness-adjustable damping enabling an adaptation to the type of walking desired by the patient, such as athletic walking or city walking.

Figure 2:
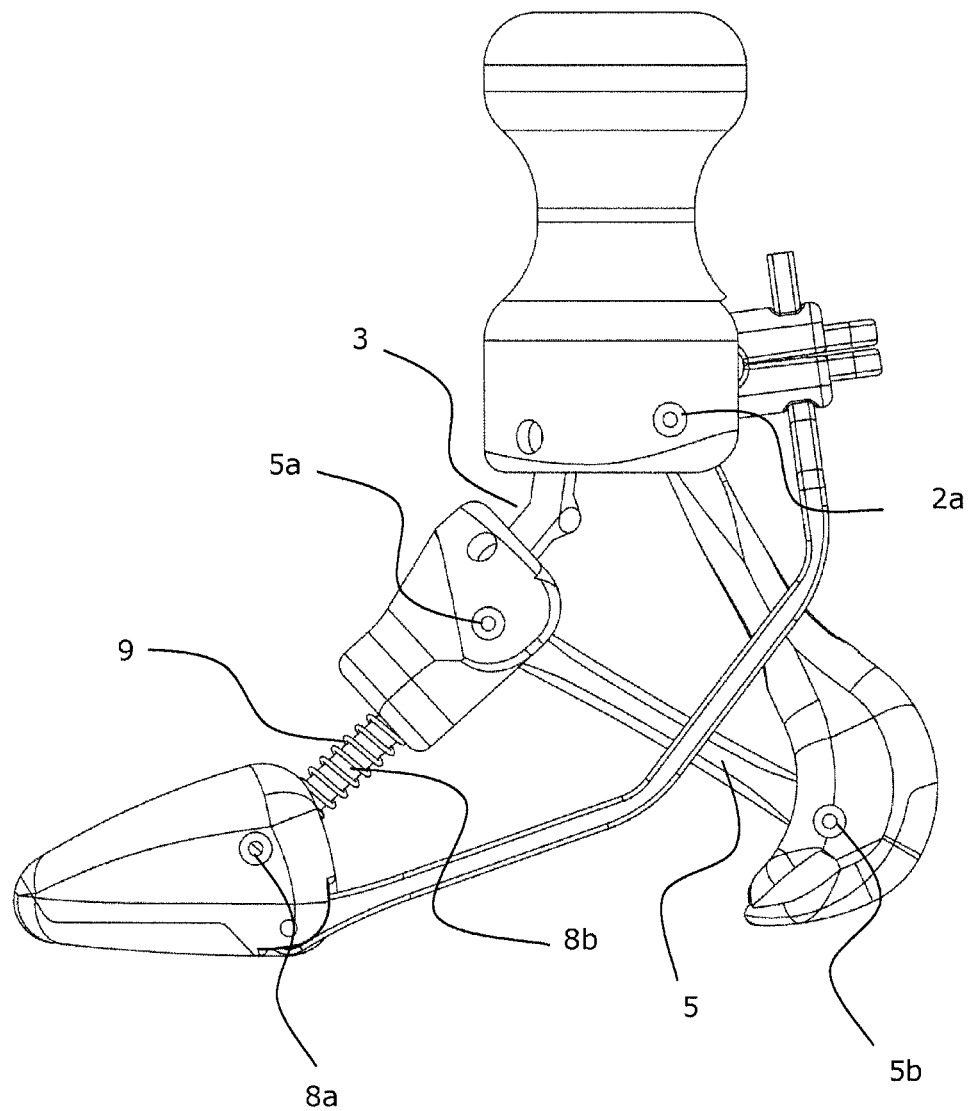
FIG. 2 is a side view of the prosthesis represented in FIG. 1.
Figure 3:
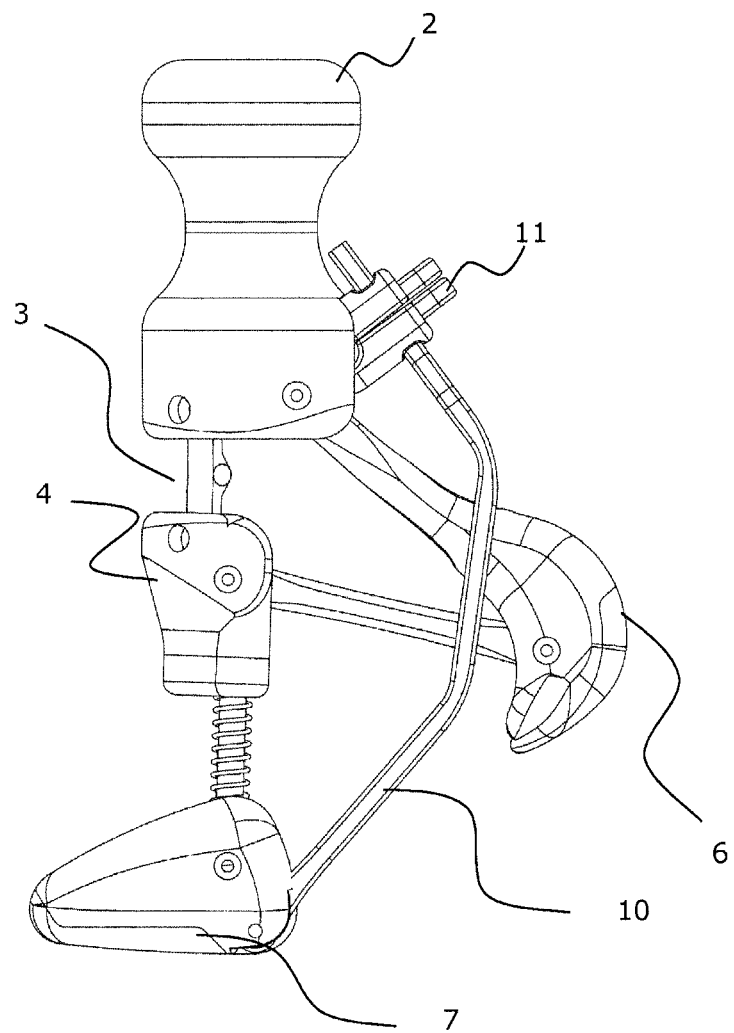
FIG. 3 is a side view of the prosthesis represented in FIG. 1 configured to receive a high heeled shoe.
Figure 4:
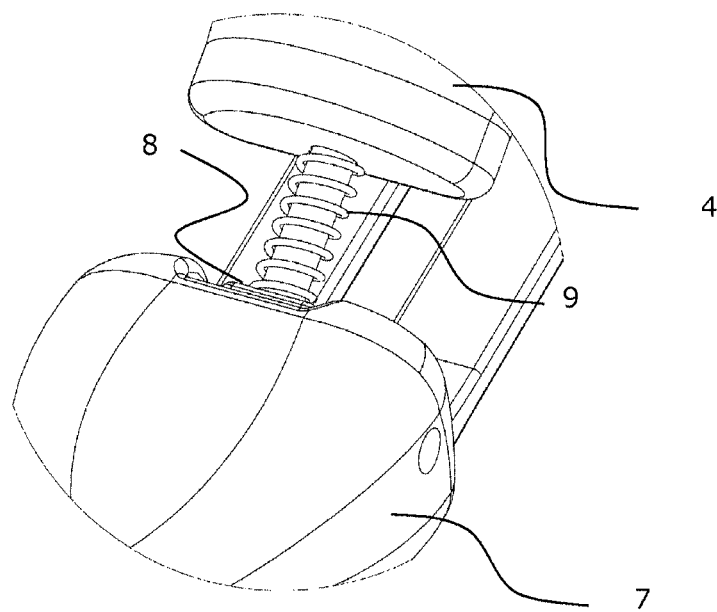
FIG. 4 is a detail view of a mechanism of the prosthesis shown in FIG. 1.

The foot prosthesis 1 further comprises a blade 10 made of composite material, of carbon fibre type, enabling a damping during the bearing phase of the heel and an accumulation of energy. In another embodiment, the blade 10 may be made of an aluminium alloy, spring steel, or any other material having mechanical characteristics making it possible to accumulate and to restore energy. The blade 10 is connected to the foot tip 7 by means of a hinge 12 of pivot link type and to the ankle support through an adjustment system 11 in which the end 10*a* of the blade 10 is housed. The adjustment system 11, comprising a mechanical locking, makes it possible to adjust the dorsiflexion and plantar flexion angles, the inversion-eversion angle, the angle of the foot tip 7 with respect to the horizontal as well as the height of the foot prosthesis. This adjustment is made by unlocking the adjustment system 11 and thereby temporarily releasing the blade 10, which can thereby translate from bottom to top and also move angularly with respect to the longitudinal axis of the ankle 2. It is then possible to adjust the angle of inclination of the instep 4, the height of the heel 6, thereby replicating plantar flexion, and the angle of inclination of the foot tip 7 with respect to the ground. The adjustment system 11 thereby allows a fine adjustment adapted to the patient and to the criteria of use, comfort and environment. FIG. 2 represents the foot prosthesis 1 adjusted to wear a low heeled shoe, the heel 6 being in a low position. FIG. 3 represents the same foot prosthesis as that seen in FIG. 2, but adjusted so that the patient can wear a high heeled shoe. In the embodiment described in FIGS. 1 to 5, a blade 10 is represented, in the form of a downwards oriented Y, comprising a first arm situated outside the foot prosthesis 1 and a second arm situated inside the foot prosthesis 1. The third branch of the Y forming the blade 10 is housed in the adjustment system 11. In another embodiment of the invention, the blade 10 may be constituted of a single blade. In yet a different embodiment, the adjustment system comprises a first actuator making it possible, in real time, to adjust the height of the blade 10 with respect to the ground and a second actuator making it possible to adjust the inclination of the blade 10 with respect to the horizontal. These actuators may be, for example, electric motors or servomotors. Force sensors are positioned at the level of the heel 6, the foot tip 7, the spring 9 and on the blade 10. The information coming from these sensors is processed in real time by a computer in order to regulate the adjustment of the foot prosthesis 1 by means of the adjustment system 11. In this embodiment, it is not necessary that the patient intervenes in the adjustment of the foot prosthesis 1 when walking conditions change, the optimal adjustment being made directly by the adjustment system 11. The blade 10 is configured so as to be distant from the ground in order not to be in contact with the latter. This procures the advantage of avoiding wear by friction of the blade 10 and thereby of greatly increasing the lifetime of the foot prosthesis 1.

The operation of the foot prosthesis 1 will now be described when a step is taken by the patient, or by a robot when the latter comprises a foot prosthesis 1. Firstly, the heel 6 comes into contact with the ground transmitting a force through the tie rod 5 to the blade 10 which deforms so as to accumulate energy and to dampen the step. The tie rod 5 also transmits a force, directed towards the heel 6, into the instep 4 which has the effect of bringing the foot tip 7 towards the ground through the universal joint 8. The spring 9 is compressed and also accumulates energy. The foot prosthesis 1 thereby generates a stabilisation effect on the inversion-eversion, even in the case of ground having a considerable banking or a protuberance such as a descent, a rise or a pebble.

When the patient, or the robot, lifts the foot prosthesis 1, to make the next step, the energy accumulated in the blade 10 and the spring 9 is restored in order to aid the patient, or the robot, to lift the foot prosthesis 1. The patient, or the robot, thereby regains an energy restoration similar to that of a human foot.

It should be noted that the various parts constituting the foot prosthesis 1 according to the invention are to be adapted, notably in dimensions, as a function of the parameters of the patient, or of the robot, receiving the prosthesis such as the weight, size or type of walk thereof.

Figure 6:
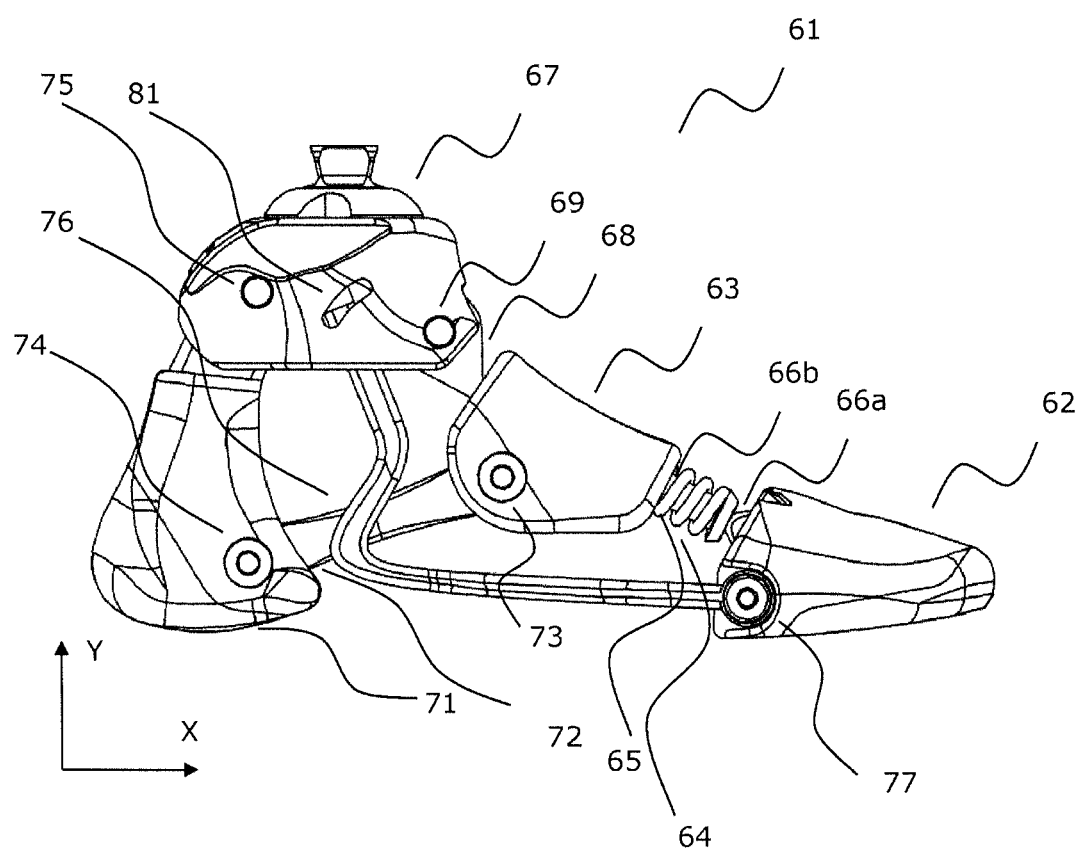
FIG. 6 represents a side view of another embodiment of the foot prosthesis according to the invention.

With reference to FIG. 6, another embodiment of a prosthesis according to the present invention is represented in a schematic manner. A foot prosthesis 61 may be seen therein comprising a foot tip 62 and an instep 63 connected together by a universal joint type link 64. The universal joint 64 comprises a first hinge 66*a* of pivot link type integrated in the foot tip 62 and a second hinge 66*b*, also of pivot link type, integrated in the instep 63. The stem of the second hinge 66*b* further comprises a spring 65. In FIG. 6 may be seen an axis X and an axis Y, perpendicular to each other. The hinge 66*a* has its axis of rotation perpendicular to the plane X-Y formed by the axes X and Y and the hinge 66*b* has its axis of rotation perpendicular to the axis of rotation of the hinge 66*a*. The spring 65 has the same function as in the embodiment described in FIGS. 1 to 5. It may also be advantageously replaced by a hydraulic, pneumatic or oleo-pneumatic dampener, or any other means making it possible to obtain stiffness-adjustable damping in order to adapt to a desired type of walking. Moreover, the instep 63 is connected to an ankle support 67 through a link 68. The link 68 comprises a first axis 69 perpendicular to the plane X-Y forming a first pivot link with the ankle support 67 and a second axis 70 (not visible) also perpendicular to the plane X-Y, forming a second pivot link with the instep 63. The link 68 is made of a single piece thereby making it possible to stiffen the foot prosthesis 61. The instep 63 is also connected to a heel 71 through a connecting rod 72. The connecting rod 72 comprises a first pivot link 73 connecting it to the instep 63 and having its axis of rotation perpendicular to the plane X-Y and a second pivot link 74 connecting it to the heel 71 also having its axis of rotation perpendicular to the plane X-Y. The heel 71 is hinged with respect to the ankle support 67 by means of a pivot link 75. The prosthesis 61 also comprises a damping element 76 directly connecting the foot tip 62 to the ankle support 67. This damping element 76 constitutes an alternative to the blade 10 of the foot prosthesis 1 such as shown in FIG. 1. The damping element 76 is configured so as to be distant from the ground in order not to be in contact with the latter. This procures the advantage of avoiding wear by friction of the damping element 76 and thereby of greatly increasing the lifetime of the foot prosthesis 61.

Figure 7:
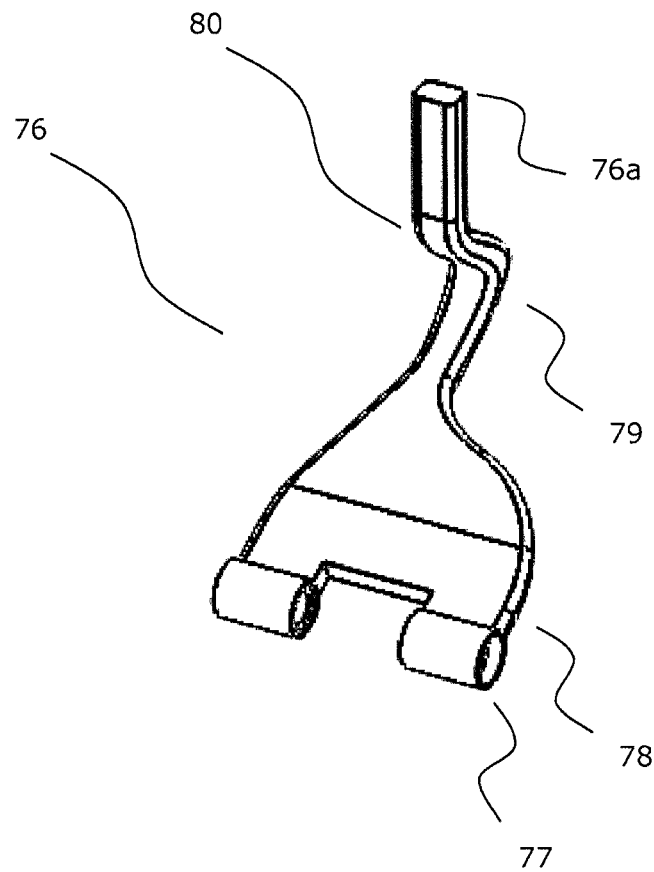
FIG. 7 represents a perspective view of a damping element of the foot prosthesis shown in FIG. 6.

With reference to FIG. 7, the damping element 76 is represented schematically and in perspective. It comprises a part 78, forming a plane, connected to the foot tip by a pivot link 77. The damping element 76 further comprises a first curvature point 79 and a second curvature point 80. This shape comprising two curvature points has the advantage of improving vertical damping. The material of the damping element 76 may be metal, for example steel, or a polymer or any other material enabling damping and accumulation of energy during the bearing on the ground of the prosthesis 61 and the walking of the patient or of the robot. The damping element 76 further comprises one end 76a that is housed in an inner adjustment means 81 of the prosthesis 61. The inner adjustment means 81 comprises a mechanical locking, such as for example a set screw. When it is wished to adjust the foot prosthesis 61, the inner adjustment means 81 is unlocked to make it possible to displace the damping element 76. In another embodiment, the adjustment means comprises an actuator making it possible to adjust the damping element 76 directly using information coming, for example, from a computer. This actuator may be, for example, an electric motor or a servomotor.

As already mentioned, the foot prosthesis that is the subject matter of the invention may also be implemented in the robotics field. Indeed, artificial feet are used therein in order that humanoid robots can walk in a manner similar to that of a human being. These robot feet are generally constituted of a simple bearing plate which can be advantageously replaced by the foot prosthesis 1 or the foot prosthesis 61. A foot prosthesis according to the invention may also be directly incorporated in the robot during its manufacture.

One of the advantages of the invention is that the blade 10 or the damping element 76 are not in contact with the ground thereby enabling a significant increase in its lifetime compared to protheses of the prior art comprising a blade directly in contact with the ground thereby undergoing permanent friction and thus rapid wear. Another advantage of the invention, compared to existing blade prostheses, is that it is not necessary to add a sock, for example made of silicone, in order to protect the prosthesis from external nuisances, such as dust, and also to reproduce the shape of a human foot.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A foot prosthesis comprising a heel and a foot tip capable of bearing on the ground and an ankle support wherein the foot prosthesis further comprises at least one damping element, an instep connecting the foot tip to the ankle support, and an elongated connecting rod connecting the instep to the heel, wherein the at least one damping element extends between and contacts the foot tip and the ankle support, and wherein a first end of the connecting rod is pivotably connected to the instep and a second end of the connecting rod is pivotably connected to the heel.

2. The foot prosthesis according to claim 1 wherein the damping element is pivotably connected to the foot tip and adjustably connected to the ankle support.

3. The foot prosthesis according to claim 1 wherein the foot prosthesis further comprises a spring for accumulating and restoring energy arranged between the foot tip and the instep.

4. The foot prosthesis according to claim 1 wherein the damping element comprises a first curvature point and a second curvature point.

5. The foot prosthesis according to claim 1 wherein the damping element comprises one end connected to the ankle support by the outside of the foot prosthesis.

6. The foot prosthesis according to claim 1 wherein the damping element comprises one end connected to the ankle support by the inside of the foot prosthesis.

7. A robot wherein the robot comprises a foot prosthesis according to claim 1.

8. The foot prosthesis according to claim 1, wherein the damping element includes a composite fiber material.

9. The foot prosthesis according to claim 1, wherein the damping element includes a first arm extending alongside a first side of the instep and a second arm extending alongside a second side of the instep, opposite to the first side.

10. The foot prosthesis according to claim 1, wherein the instep is connected to the foot tip through a universal joint.

11. The foot prosthesis according to claim 1, wherein the instep includes a stiffness-adjustable dampener.

12. The foot prosthesis according to claim 1, wherein the connecting rod is configured to transmit force from the heel to the instep.

13. The foot prosthesis according to claim 1, wherein the connecting rod is connected to the instep at an intermediate point between the connection of the instep to the ankle support and the connection of the instep to the foot tip.

14. The foot prosthesis according to claim 1, wherein the heel is pivotably connected to the ankle support.

15. The foot prosthesis according to claim 1, wherein the instep includes a first pair of tie rods hinged around a first pivot link and a second pair of tie rods hinged around a second pivot link.

16. The foot prosthesis according to claim 1, wherein the at least one damping element is configured to be distant from said ground.

17. A foot prosthesis comprising a heel and a foot tip capable of bearing on the ground and an ankle support wherein the foot prosthesis further comprises at least one damping element configured to be distant from said ground, an instep connecting the foot tip to the ankle support, and a connecting rod connecting the instep to the heel, wherein the at least one damping element extends between and contacts the foot tip and the ankle support, wherein the ankle support further comprises an adjustment system configured to receive an end of the damping element and configured to adjust the length and/or orientation of the damping element relative to the ankle support.

18. The foot prosthesis according to claim 17, wherein the adjustment system is configured to adjust the dorsiflexion angle, the plantar flexion angle, the inversion-eversion angle, the angle of the foot tip with respect to the horizontal, and/or the height of the foot prosthesis.

19. The foot prosthesis according to claim 18, wherein the adjustment system includes a first actuator configured for adjusting the height of the foot prosthesis and/or a second actuator configured for adjusting the inclination of the damping element with respect to the horizontal.

20. The foot prosthesis according to claim 19, further comprising force sensors located at the heel, the foot tip, the instep and/or the damping element, wherein said force sensors providing information used by the adjustment system to real-time regulate the position of the damping element relative to the ankle support.

* * * * *